United States Patent [19]
Norton

[11] Patent Number: 5,137,033
[45] Date of Patent: Aug. 11, 1992

[54] PATIENT MONITORING DEVICE
[76] Inventor: John L. Norton, 449 Park Ave., Pocatello, Id. 83201
[21] Appl. No.: 730,046
[22] Filed: Jul. 15, 1991
[51] Int. Cl.$^5$ .......................... A61F 5/37; G08B 23/00
[52] U.S. Cl. ..................................... 128/886; 340/573
[58] Field of Search ................ 128/885, 886; 340/235, 340/279, 573, 604, 603, 620; 200/61.05, 61.04

[56] References Cited
U.S. PATENT DOCUMENTS

| | | | |
|---|---|---|---|
| 2,866,454 | 12/1958 | McKenzie | 128/886 |
| 2,907,841 | 10/1959 | Campbell | 128/886 |
| 3,460,123 | 8/1969 | Bass | 128/886 |
| 3,810,140 | 5/1974 | Finley | 128/886 |
| 3,971,371 | 7/1976 | Bloom | 128/886 |
| 4,163,449 | 8/1979 | Regal | 128/886 |
| 4,178,589 | 12/1979 | Nunn | 128/886 |
| 4,271,406 | 6/1981 | Wilson | 128/886 |
| 4,356,479 | 10/1982 | Wilson | 128/886 |
| 4,800,370 | 1/1989 | Vetecnik | 128/886 |
| 5,036,859 | 8/1991 | Brown | 128/886 |

Primary Examiner—Michael A. Brown
Attorney, Agent, or Firm—M. Reid Russell

[57] ABSTRACT

A patient monitoring device for notifying through an alarm, a nurse or health care provider of a wet or distressed condition of a patient that involves a detecting pad for a bed or wheelchair to conduct an electric current when wet with urine. The monitoring device that is hard wired in one embodiment to provide for alerting a nurse at a nurses station of a bed ridden patient's wet condition and in a wheelchair embodiment to notify through a ratio linkage, a nurse of patient's wet condition or that the wheelchair has tipped over.

9 Claims, 2 Drawing Sheets

PATIENT MONITORING DEVICE

BACKGROUND OF THE INVENTION

1. Field of the Invention

This invention relates to devices that provide an alarm to notify medical personnel of a bed wetting occurrence or other emergency situation as a patient may encounter.

2. Prior Art

There are a number of liquid sensing devices involving configurations of electrically operated liquid sensing arrangements where the presence of urine creates an electrical connection to an alarm device. Examples of such earlier devices are shown in U.S. Patents to: Seiger, U.S. Pat. No. 2,644,050; Kroening et al, U.S. Pat. No. 2,726,294; Fendole et al, U.S. Pat. No. 4,069,817; Hatfield, U.S. Pat. No. 4,020,478; Regal, U.S. Pat. No. 4,163,449; and Uyehara, U.S. Pat. No. 4,347,503.

The above U.S. patents are directed towards devices for sensing the liquid presence between conductor elements positioned under a patient. Along with liquid sensing arrangements each involves connecting a power source through the liquid sensing arrangement to complete an electrical circuit to an alarm device for alerting a health care provider to the patient's wet condition. In a patent to Wilson, U.S. Pat. No. 4,271,406, a liquid presence sensing circuit is hard wired to a nurse's station alarm to alert that station that liquid is present in a patient's bed. Neither this arrangement, nor the other cited earlier patents, however, involves either a removable mattress pad with strip conductor that is easily changed and reconnected into a circuit, which reconnection resets a relay thereof, or a radio transmitter and receiver system as taught by the present invention.

Further unique to the present invention it is also applicable for use with a wheelchair and includes tilt sensing of that wheelchair for alerting health care personnel to the wheelchair tipping over.

SUMMARY OF THE INVENTION

It is a principal object of the present invention to provide a patient liquid detection device for sensing the presence of moisture, particularly urine, and alerting a health care provider that their attention is needed to the patient.

Another object of the present invention is to provide, as a liquid sensing arrangement, a sandwich of conductive strips between a water absorbing pad as the electrodes that are contained within a disposable mattress cover, a urine presence to complete an electrical connection between a power source and an alarm that is locked in by a relay, which relay is reset by replacement of the mattress pad.

Another object of the present invention is to provide a monitoring device that will automatically sense urine presence in a mattress or seat cover and operate an alarm circuit that is linked by hard wire, or by a radio transmitter, to be received by a health care provider.

Still another object of the present invention is to provide a patient monitoring device for both sensing moisture presence and further providing an emergency alerting capability where, should a patient seated on a monitoring device, such as a wheelchair, that has tipped over, that condition will also alert a nurse or other health care provider, through a radio transmitter, to the condition of that patient.

Still another object of the present invention is to provide a disposable urine sensing arrangement as part of a disposable mattress or seat cover that is easily removed and replaced.

The present invention is in a patient monitoring device for detecting moisture presence, particularly urine, in a pad that the patient either rests on or is seated upon. The moisture detection device is arranged in a cover as strip conductors that are separated by a liquid absorbing divider. Which detection device, when wet with urine, completes an electrical circuit therethrough. The urine presence completes an electrical circuit connection that is locked in through a relay that is not released until the moisture detector is removed and replaced. The alarm signal can be passed through a hard wire system to a nurse's call light, or can be arranged to automatically activate a nurse's paging system.

The moisture detector of the present invention is sandwiched of at least two conductive stripes separated by a divider, preferably a fiber medium that is electrically conductive when wet with urine. A circuit is formed through the wet pad from a power source, that can be battery or transformer, that provides a low voltage presence at the conductor pads.

The moisture sensing pad can be formed as part of a disposable mattress cover, wheelchair seat pad, or the like. For the mattress pad, it can be hard wired through the relay to a nurse's call station. For the wheelchair pad, it can be connected through the relay to a radio transmitter that broadcasts on a designated frequency to be received at a nurse's station receiver, the transmitted signal alerting the nurse to the patient's condition. Further, with the wheelchair pad arrangement, a tilt switch is included as part of the electrical circuitry, to alert the health care provider should the chair be tipped over or is not aligned with the vertical.

In both of the bed and wheelchair embodiments, the voltage as the patient could be exposed to is very low so as not to create a problem from a patient's physical contact therewith.

IN THE DRAWINGS

In the drawings it will be illustrated that which is presently regarded as the best mode for carrying out the invention:

Figure 3:
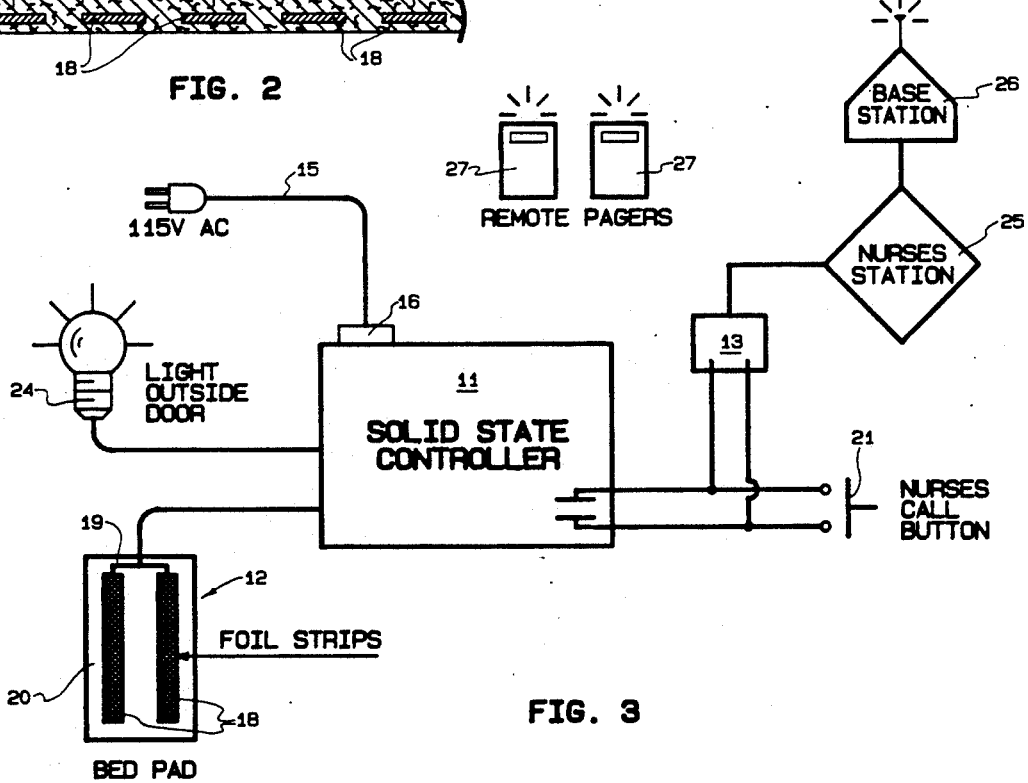
Figure 4:
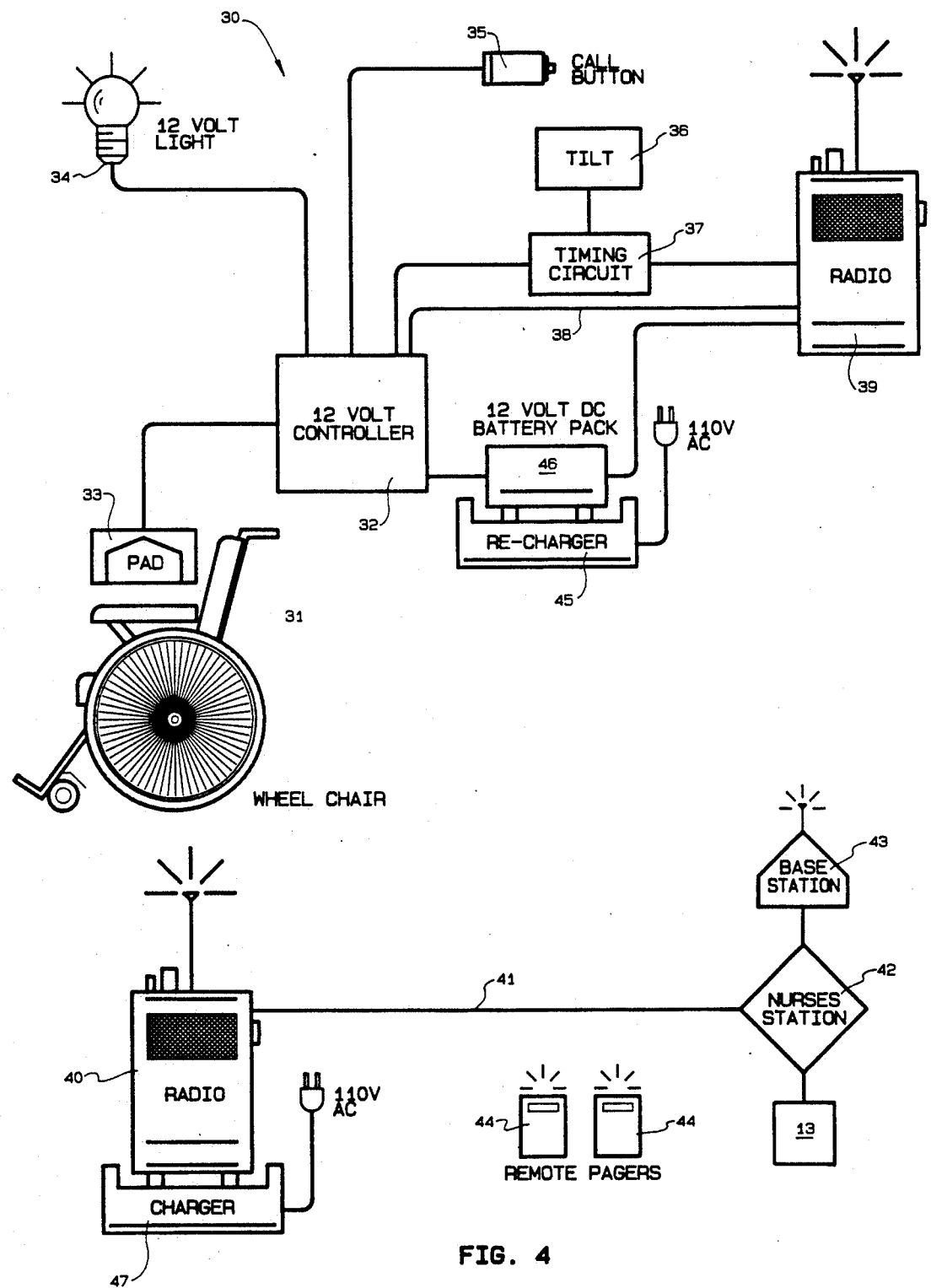

FIG. 3, shows a schematic of the urine monitoring device arranged as a bed pad with a controller that is hard wired to the nurse's station; and FIG. 4, shows a schematic of a wheelchair version of the monitoring device of the present invention that incorporates the controller and includes a separate radio transmitter to broadcast to a receiver at the nurse's station, and further includes a tilt switch arrangement.

DETAILED DESCRIPTION

Figure 1:
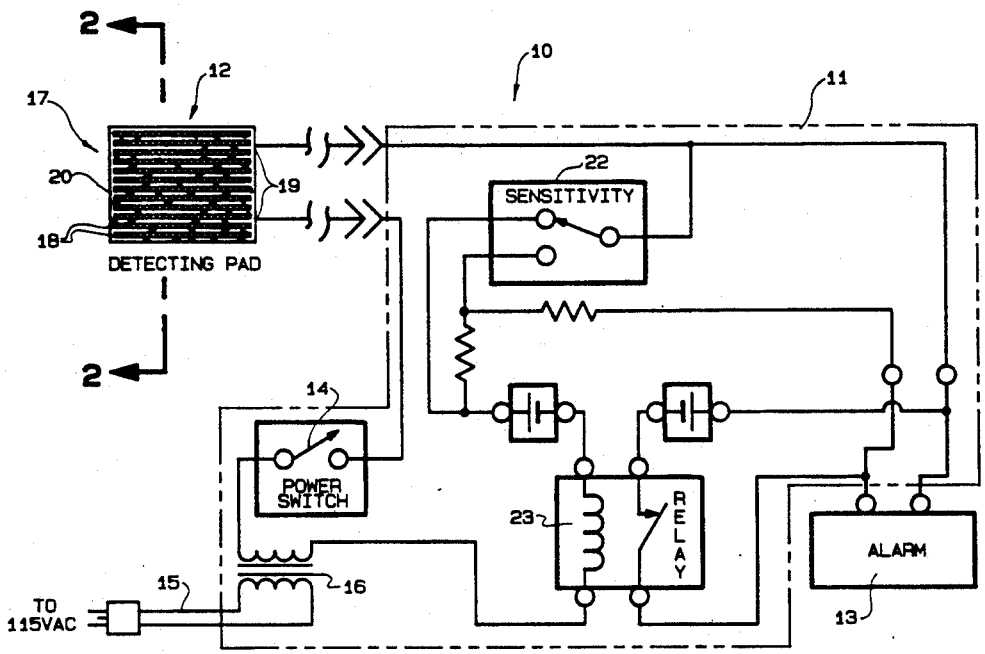
FIG. 1, shows a schematic view of the monitoring device of the present invention as including a urine detecting pad that is a sandwich of electrical conductive stripes separated by a fiber pad, the conductive stripes shown in circuit with a power source and relay and is hard wired to an alarm at a nurse's station and to a radio transmitter at that nurse's station.

Shown in FIG. 1 is a block flow schematic of the present invention in a patient monitoring device 10, hereinafter referred to as monitoring device. The monitoring device 10 is shown as consisting of a solid state controller 11, hereinafter referred to as controller, that receives a sensing of the presence of ion rich liquid, such as human urine, from a closing of a circuit through a detecting pad 12 to operate an alarm 13. The controller 12 is powered through an off/on power switch 14 from an electrical power source, shown herein as a 115 Volt A.C. cable and plug 15, that is transformed by a transformer 16 to 12 Volts. That voltage is then passed through the on/off power switch 14 to operate the controller.

Operation of the power switch 14 energizes the controller making electrical power available to detecting pad 12. The detecting pad 12 is for positioning beneath a bed ridden patient, and consists of detecting pad sections 17 of a plurality of conductive strips 18 that are connected by wires 19 in parallel. The conductive strips 18 can be formed of metal foil or like conducted material and are arranged parallel to one another with open areas therebetween. The detecting pad sections 17 of detecting pads are separated by a non-conductive pad 20 within an outside water permeable cover, hereinafter referred to as pad. The pad 20 is itself non-conductive but will become conductive when wet with urine, or other ion rich liquid. Pad 20 is sandwiched between detecting pads sections 17 that are identical and are each connected to the controller 11.

The detecting pad 12 connects to the controller 11, first to a sensitivity relay 22 that, upon sensing conductivity through the detecting pad 12, closes to pass current through a diode 24 to a relay 23. Which relay 23 will lock in a conducting attitude and remain locked until reset. Which resetting, for the present invention, involves replacing the wet detecting pad 12 with a dry detecting pad.

Figure 2:
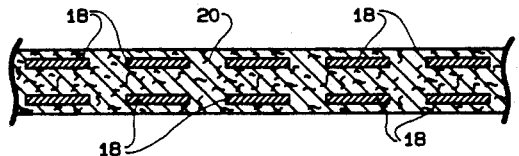
FIG. 2, shows a sectional view of the urine detecting pad taken along the line 2—2 of FIG. 1.

FIG. 2 shows a preferred example of the detecting pad 12 as consisting of parallel spaced sections 17 of the conductive stripes 18 connected at their ends in parallel by wires 19, and are separated by a layer or pad 20 of absorbent material that is non-conductive. Urine, as would be absorbed in the pad 20 of absorbent material will provide an ion source to cause the absorbent material to conduct a current across the respective conductive strips 18. This completes the circuit between the power supply to the alarm 13. In practice, the detecting pad strips 18 are cut to be of equal width and length parallel and are connected at their head ends, with the pad 20 of liquid absorbtion material arranged between the individual strips 18 and detecting pad sections 17.

FIG. 3 shows the monitoring device 10 as further including a light 24 that is mounted outside of a patient's room. Such light, however, could be remote light as on a remote indicator panel as at a nurse's station. The illumination of which light 24 is connected in parallel to the alarm circuit such that, when the alarm circuit is energized, the light 24 will also turn on. Which energizing of the alarm circuit, shown in FIG. 3, may also be operated by depressing a typical nurse's call button 24 that connects to the nurse's station 25 or, could involve a transmission of a signal from a base station 26 to remote pagers 27 that nurses carry.

FIG. 4 shows another embodiment of the present invention in a patient monitoring device 30, hereinafter referred to as monitoring device. The monitoring device 30 is intended for use by a patient who is in a wheelchair 31. It includes a solid state controller 32, hereinafter referred to as controller, that is essentially the same as controller and connects to a detecting pad 33. The detecting pad 33 is essentially like detecting pad 12 as shown in FIGS. 1 through 3, except it is dimensioned to fit on the seat of a wheelchair 31. The controller 32 includes a 12 Volt light 34 that is for illuminating to indicate a urine presence in detecting pad 33.

Further to the monitoring device 30, it preferably includes a call button 35 that is accessible to a patient seated in the wheelchair 31 that is for notifying a nurse's station that help is needed. Such call button can be like call button 21, which is standard in a hospital setting, except that call button 35 operates an alarm through a radio transmission, as set out below.

Further, to the monitoring device 30, it preferably includes a tilt switch 36 that, should the chair be tilted beyond a set angle, such as a thirty (30) to forty-five (45) degrees, the tilt switch is energized to start a timing circuit 37. Should the tilt condition not be corrected before the timing circuit times out, that tilt condition will cause the controller 32 to operate an alarm.

Controller 32 upon receiving notice of an ion rich liquid presence in detecting pad 33, by operation of call button 35, or by receiving notice that the wheelchair 31 is tilted from tilt switch 36 passed through timing circuit 37, passes an alarm signal through a line 38 to a radio transmitter 39. The radio transmitter, is a low power transmitter that transmits to a receiving radio station 40 at a nurse's station 42. This signal sets off alarm 13. Further, notice of the alarm can be passed as a signal from a base station to remote pagers 44 carried nurses. Alarm 13 in this embodiment, is like that arrangement as set out with respect to FIGS. 1 through 3 and may include a light presence, operate a buzzer or the like. The system may or may not, as desired, utilize a base station 43 and remote pagers 44.

As shown, the system of controller 32 and radio transmitter 39 are preferable a twelve (12) Volt system. For supplying that voltage to the wheelchair portion of the system, a charger 45 is provided that connects by a cord and plug to a 110 Volt A.C. source, which charger transforms that voltage to twelve (12) Volts and connects it to a battery pack 46 that is included as part of the monitoring device 30. Similarly, radio 40 that is located at the nurse's station 42, preferably also includes a charger 47 that may be self-contained and includes a battery portion, which charger 47, as shown, is preferably arranged for recharging through a conventional cable and 112 Volt A.C. plug.

Hereinabove have been set out two embodiments of monitoring devices 10 and 30, respectively, both for alerting a nurse or health care worker to a wet or emergency condition of a patient either in a bed or in a wheelchair.

Although preferred forms of my invention have been disclosed herein it should be understood that the present disclosure is made by way of example only and that variations are possible without departing from the subject matter coming within the scope of the following claims and reasonable equivalency thereof, which subject matter I regard as my invention.

I claim:

1. A patient monitoring device comprising, a detecting pad means that includes electrically conductive sections separated by a non-conductive material that will become conductive when wetted with human urine and is of a shape to allow it to be arranged as a wheelchair seat pad; a system power supply; a controller connected for receiving electrical power when said detecting pad means is in a conductive state that includes a locking relay that, on receipt of electrical power, can be reset only when the conducting detecting pad means is removed and replaced with a non-conducting detecting pad means, said controller is connected to a transmitter means to transmit an alarm signal to an alarm means located at a nurse station; and alarm means that is operated on receipt of said alarm signal from said controller.

2. A patient monitoring device as recited in claim 1, wherein the detecting pad means is made up of a pair of electrically conductive sections consisting of individual conductive strips that for each section are connected in parallel, and are separated by a pad of fabric material that is electrically non-conductive when dry and becomes electrically conductive when wet with urine.

3. A patient monitoring device as recited in claim 1, further including a sensitivity switch within the controller whereon sensing a certain minimum voltage presence at the detecting pad means the sensitivity switch operates to conduct current to the relay.

4. A patient monitoring device as recited in claim 1, wherein the alarm means is an audio alarm and light.

5. A patient monitoring device as recited in claim 4, further including a base station operated by the alarm means to transmit a signal to a nurse's pager.

6. A patient monitoring device as recited in claim 1, further including a call button means for patient operation hard wire connected through the controller to operate the alarm means when activated.

7. A patient monitoring device as recited in claim 1, further including, with the controller a timer circuit and tilt switch means for sensing a displacement of a wheelchair, wherein the detecting pad means is arranged as a seat, from the vertical that, after a passage of a set period of time, operates the controller to transmit the alarm signal to operate the alarm means at the nurses station.

8. A patient monitoring device as recited in claim 7, further including a call button means wired to the controller for the patient to depress to cause the controller to transmit the alarm signal to the nurses station receiver.

9. A patient monitoring device as recited in claim 7, wherein the nurses station receiver is connected to a base station to transmit a signal to a nurse's pager on receipt of an alarm signal.

* * * * *